(12) United States Patent
Kojima

(10) Patent No.: US 10,595,708 B2
(45) Date of Patent: Mar. 24, 2020

(54) CONTROL DEVICE FOR ENDOSCOPE SYSTEM, ENDOSCOPE SYSTEM, AND CONTROL METHOD FOR ENDOSCOPE SYSTEM

(71) Applicant: OLYMPUS CORPORATION, Hachioji-shi, Tokyo (JP)

(72) Inventor: Koji Kojima, Koganei (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/644,958

(22) Filed: Jul. 10, 2017

(65) Prior Publication Data

US 2017/0303768 A1    Oct. 26, 2017

Related U.S. Application Data

(63) Continuation of application No. PCT/JP2016/079848, filed on Oct. 6, 2016.

(30) Foreign Application Priority Data

Oct. 30, 2015  (JP) .................................. 2015-214564

(51) Int. Cl.
    A61B 1/06       (2006.01)
    A61B 1/045      (2006.01)
    (Continued)

(52) U.S. Cl.
    CPC ...... *A61B 1/00006* (2013.01); *A61B 1/00009* (2013.01); *A61B 1/00045* (2013.01);
    (Continued)

(58) Field of Classification Search
    CPC ... A61B 1/00006; A61B 1/00; A61B 1/00009; A61B 1/00045; A61B 1/00087;
    (Continued)

(56) References Cited

U.S. PATENT DOCUMENTS

| | | | |
|---|---|---|---|
| 2004/0186351 A1* | 9/2004 | Imaizumi ........... | A61B 1/00009 600/160 |
| 2005/0107853 A1* | 5/2005 | Krespi ................... | A61B 18/18 607/89 |

(Continued)

FOREIGN PATENT DOCUMENTS

| | | |
|---|---|---|
| JP | 2009-95539 A | 5/2009 |
| JP | 2009-95559 A | 5/2009 |
| JP | 2015-119891 A | 7/2015 |

OTHER PUBLICATIONS

May 11, 2018 Translation of the IPRP issued in International Application No. PCT/JP2016/079848.

(Continued)

*Primary Examiner* — Timothy J Neal
*Assistant Examiner* — William B Chou
(74) *Attorney, Agent, or Firm* — Oliff PLC

(57) ABSTRACT

An endoscope system includes an imaging unit having an image sensor to image a subject, a light source emitting illumination light for illuminating the subject, and a laser treatment instrument which can emit laser light for treating the subject during emission of the illumination light. A control device for the endoscope system includes a determination unit which determines a state of use of the laser treatment instrument, and a brightness adjustment circuit which adjusts at least one of exposure time in imaging by the imaging unit and the amount of emitted light of the light source based on the result of determination by the determination unit.

6 Claims, 8 Drawing Sheets

(51) Int. Cl.
*A61B 18/20* (2006.01)
*A61B 1/00* (2006.01)
*A61B 1/04* (2006.01)
*A61B 18/00* (2006.01)

(52) U.S. Cl.
CPC ............ *A61B 1/00087* (2013.01); *A61B 1/04* (2013.01); *A61B 1/045* (2013.01); *A61B 1/06* (2013.01); *A61B 1/0638* (2013.01); *A61B 18/20* (2013.01); *A61B 2018/00982* (2013.01)

(58) Field of Classification Search
CPC .. A61B 1/04; A61B 1/06; A61B 1/043; A61B 1/045; A61B 1/0638; A61B 1/0661
USPC ........ 600/103, 108, 109, 113, 117, 118, 160, 600/178, 179, 180, 181, 182
See application file for complete search history.

(56) References Cited

U.S. PATENT DOCUMENTS

| | | | |
|---|---|---|---|
| 2006/0020169 A1* | 1/2006 | Sugimoto | A61B 1/00009 600/180 |
| 2007/0213588 A1* | 9/2007 | Morishita | A61B 1/043 600/156 |
| 2007/0213593 A1* | 9/2007 | Nakaoka | A61B 1/043 600/181 |
| 2009/0054881 A1* | 2/2009 | Krespi | A61B 17/22012 606/9 |
| 2009/0187176 A1* | 7/2009 | Assa | A61B 18/22 606/17 |
| 2010/0160903 A1* | 6/2010 | Krespi | A61B 17/22012 606/7 |
| 2011/0121200 A1* | 5/2011 | Watanabe | A61B 1/043 250/458.1 |
| 2012/0076434 A1* | 3/2012 | Watanabe | A61B 1/0638 382/274 |
| 2012/0123213 A1* | 5/2012 | Seto | A61B 1/0638 600/178 |
| 2013/0144281 A1* | 6/2013 | Lewinsky | A61B 18/20 606/16 |
| 2014/0031623 A1* | 1/2014 | Kagaya | A61B 1/00009 600/109 |
| 2014/0184769 A1* | 7/2014 | Ishihara | A61B 1/00009 348/68 |
| 2014/0340496 A1* | 11/2014 | Okawa | A61B 1/00006 348/65 |
| 2016/0106299 A1* | 4/2016 | Kamee | A61B 1/00006 348/67 |

OTHER PUBLICATIONS

Dec. 27, 2016 International Search Report issued in International Patent Application No. PCT/JP2016/079848.
May 24, 2018 Office Action issued in Chinese Patent Application No. 201680004734.4.

* cited by examiner

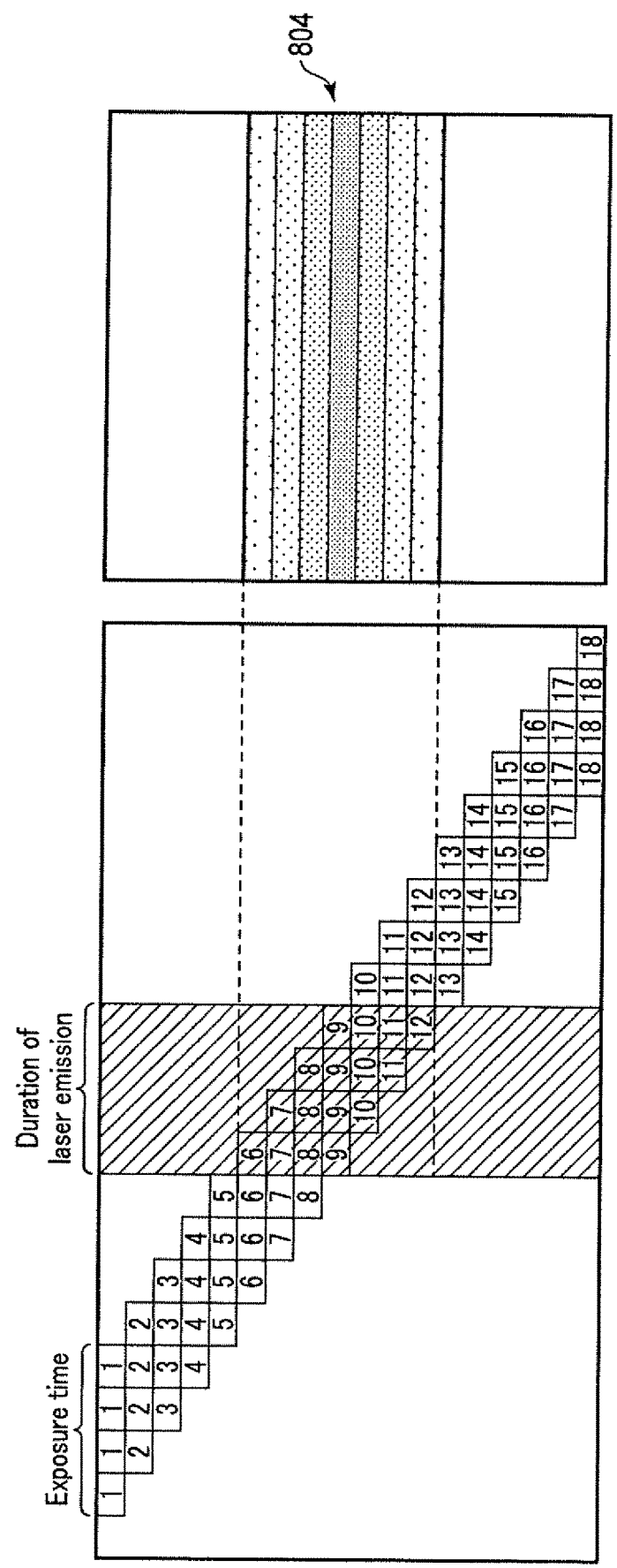
F I G. 5A

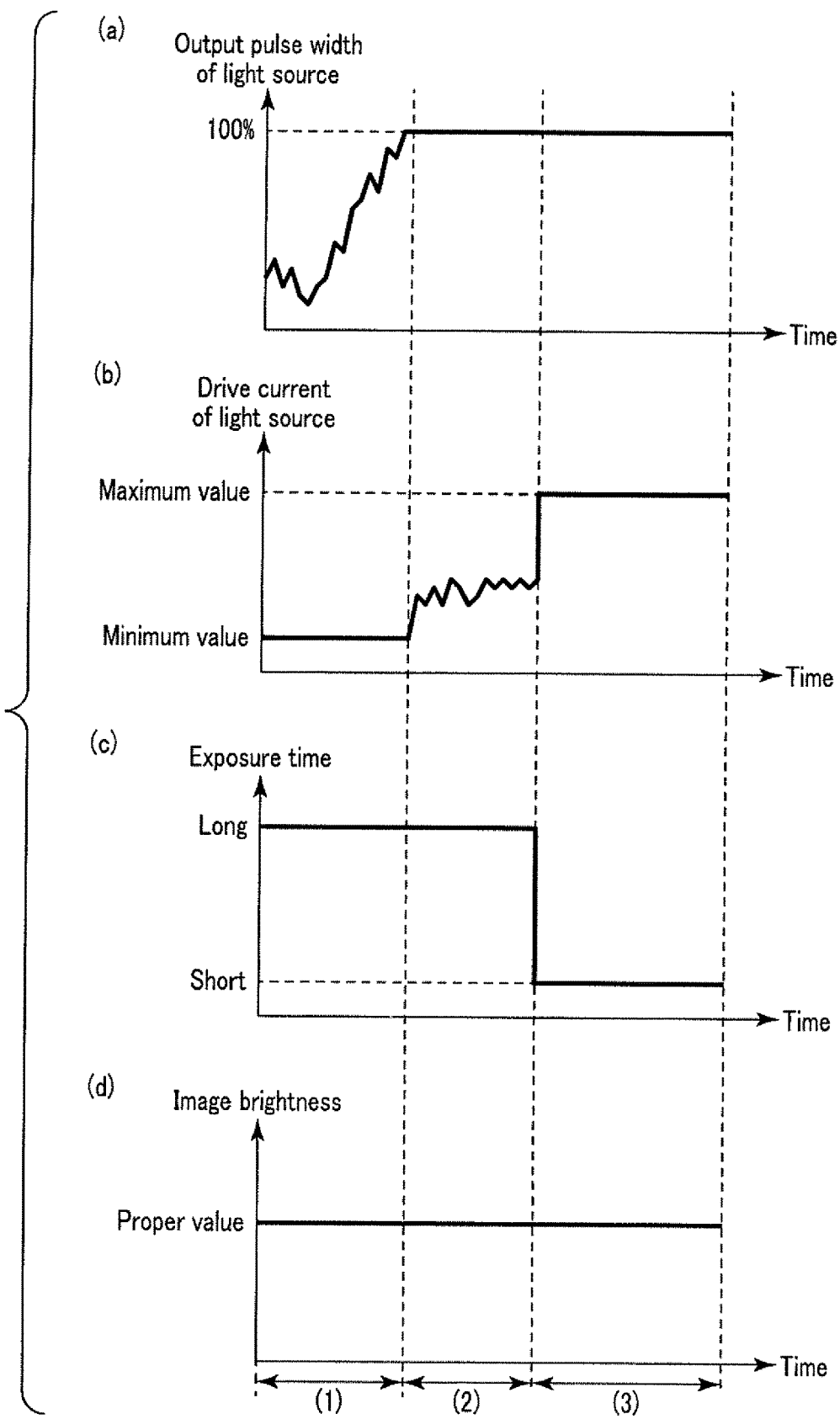
F I G. 7

CONTROL DEVICE FOR ENDOSCOPE SYSTEM, ENDOSCOPE SYSTEM, AND CONTROL METHOD FOR ENDOSCOPE SYSTEM

CROSS-REFERENCE TO RELATED APPLICATIONS

This application is a Continuation Application of PCT Application No. PCT/JP2016/079848, filed Oct. 6, 2016 and based upon and claiming the benefit of priority from prior Japanese Patent Application No. 2015-214564, filed Oct. 30, 2015, the entire contents of all of which are incorporated herein by reference.

BACKGROUND OF THE INVENTION

1. Field of the Invention

The present invention relates to a control device for an endoscope system, an endoscope system, and a control method for an endoscope system.

2. Description of the Related Art

A method has been known which treats tissue as a treatment subject by irradiating it with laser light while observing it with an endoscope. The technique for an electronic endoscope used in such treatment is disclosed in, for example, Jpn. Pat. Appln. KOKAI Publication No. 2009-095539. The endoscope disclosed therein is provided with a common light guide to guide white illumination light for observation as well as laser light for treatment. In this endoscope, either the illumination light or the treatment laser light is exclusively transmitted by the same light guide.

BRIEF SUMMARY OF THE INVENTION

In one embodiment of the present invention, a control device is a control device for an endoscope system. The endoscope system includes an imaging unit comprising an image sensor configured to image a subject, a light source configured to emit illumination light for illuminating the subject, and a laser treatment instrument capable of emitting laser light for treating the subject during emission of the illumination light. The control device comprises a determination unit which determines a state of use of the laser treatment instrument; and a brightness adjustment circuit which adjusts at least one of exposure time in imaging by the imaging unit and an amount of emitted light of the light source based on a result of determination by the determination unit.

In one embodiment of the present invention, an endoscope system comprises the control device, the imaging unit, the light source, and the laser treatment instrument as above.

In one embodiment of the present invention, a control method is a method for controlling an endoscope system. The endoscope system includes an imaging unit comprising an image sensor configured to image a subject, a light source configured to emit illumination light for illuminating the subject, and a laser treatment instrument capable of emitting laser light for treating the subject during emission of the illumination light. The method comprises determining a state of use of the laser treatment instrument; and adjusting at least one of exposure time in imaging by the imaging unit and an amount of emitted light of the light source based on a result of determining the state of use.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 5A is an illustration for explaining the effect of an electronic shutter when an image sensor is a CMOS image sensor. The figure intends to explain the relationship between exposure time and a read image when the exposure time is long.

FIG. 7 is a schematic diagram for explaining the overview of an exemplary operation of each unit in an endoscope system.

DETAILED DESCRIPTION OF THE INVENTION

One embodiment of the present invention will be described with reference to the drawings. This embodiment relates to an endoscope system that treats a subject with a laser treatment instrument while obtaining images of the subject using a medical rigid scope and an imaging device.

<System Configuration>

Figure 1:
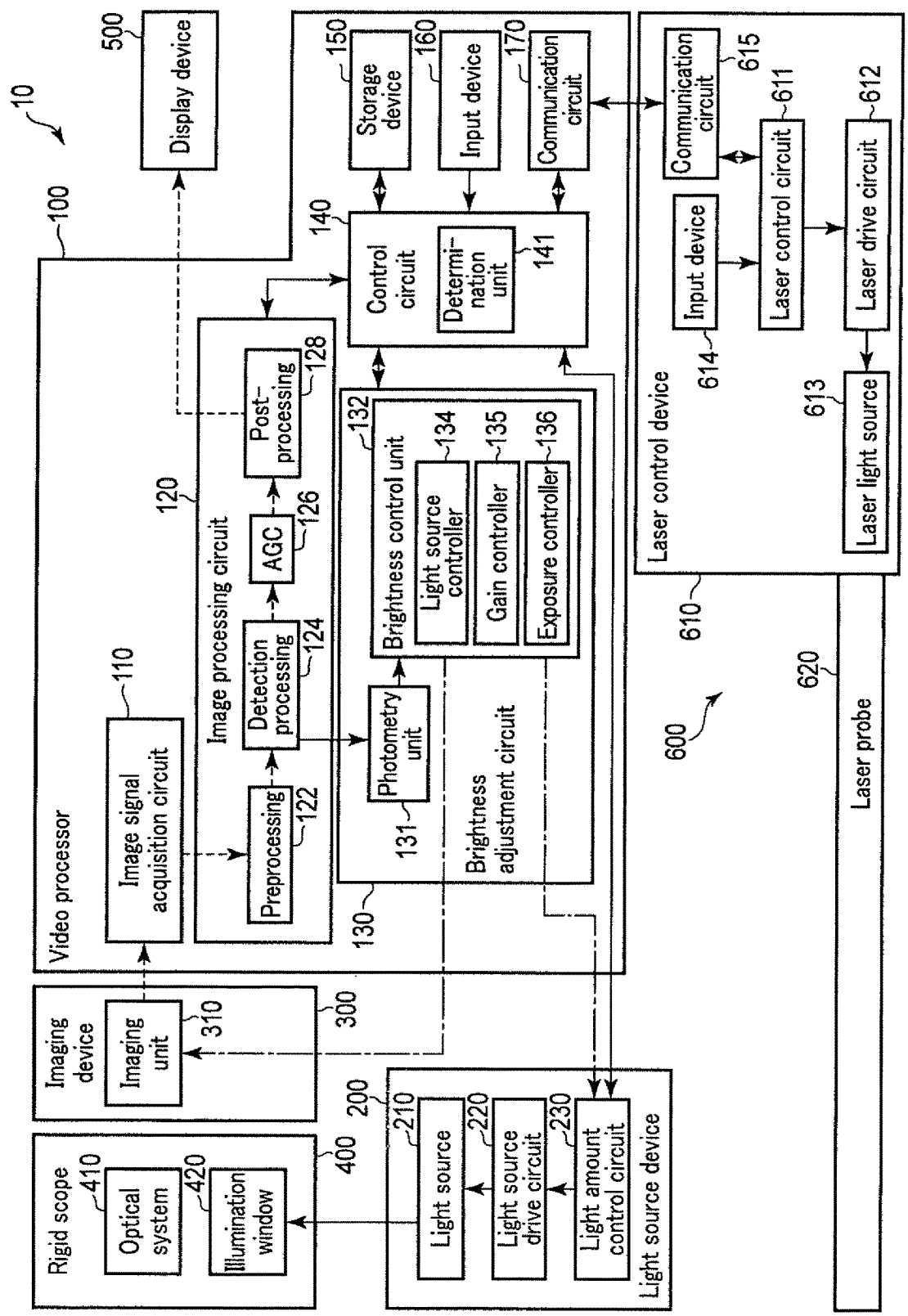
FIG. 1 is a block diagram schematically illustrating an exemplary configuration of an endoscope system according to one embodiment.

FIG. 1 schematically illustrates an exemplary configuration of an endoscope system 10 according to the present embodiment. As shown in FIG. 1, the endoscope system 10 comprises a video processor 100 that functions as a control device for the endoscope system 10, a light source device 200, an imaging device 300, a rigid scope 400, a display device 500, and a laser treatment instrument 600. In FIG. 1, the dashed arrows indicate the flow of image signals from the acquisition at the imaging device 300 to the display on the display device 500. The dashed-and-dotted arrows indicate the flow of control signals relating to the later described brightness control for adjusting the brightness of images. The solid arrows indicate the flow of signals, etc. other than these signals.

The rigid scope 400, as a general optical telescope, is configured to connect with the imaging device 300. The imaging device 300 comprises an imaging unit 310 comprising image sensor, etc. The image sensor includes, for example, a CCD image sensor or a CMOS image sensor. This embodiment assumes that the imaging unit 310 adopts a three-plate system. Note that the imaging unit 310 may adopt a single-plate system as well. If the single-plate system is adopted, synchronization processing, etc. is required. The imaging unit 310 utilizes the image sensor to generate image signals for the subject image formed on the imaging surface of the image sensor.

The rigid scope 400 comprises an optical system 410 and an illumination window 420. The optical system 410 forms an image of a subject on the imaging surface of the image sensor of the imaging device 300. The illumination window 420 is a window to emit illumination light that has been guided from the light source device 200. The illumination light emitted from the illumination window 420 illuminates the subject to be imaged by the imaging unit 310.

The light source device 200 comprises a light source 210, a light source drive circuit 220, and a light amount control circuit 230. The light source 210 emits illumination light for irradiation from the illumination window of the rigid scope 400. The light source 210 may be a lamp such as a xenon lamp or a halogen lamp, and may also be a semiconductor light source such as a laser diode or a light-emitting diode. The semiconductor light source may comprise a plurality of light sources for emitting, for example, red light, green light, and blue light, respectively, and combine them into white light. The semiconductor light source may also be a white light semiconductor light source comprising a blue light source and a fluorescent substance, and configured to emit white light by combining blue light from the blue light source with fluorescent light from the fluorescent substance, the fluorescent light having been emitted using the blue light as an excitation light. As needed, the light source 210 may comprise a light source other than the light source for preparing white light, for example, a semiconductor light source. The embodiment has assumed an example where the light source device 200 is separately provided, but this is not a limitation. For example, a white light source, etc. may be integrally provided with the video processor 100. In other words, it is also possible to provide, for example, a light source-integrated video processor having both the function of the video processor 100 and the function of the light source device 200, and the housing of this video processor may accommodate the later detailed components, i.e., an image signal acquisition circuit 110, an image processing circuit 120, a brightness adjustment circuit 130, a control circuit 140, a storage device 150, an input device 160, a communication circuit 170, the light source 210, the light source drive circuit 220, the light amount control circuit 230, etc.

The light source drive circuit 220 drives each light source in the light source 210. The light amount control circuit 230 controls the operation of the light source drive circuit 220. Specifically, the light amount control circuit 230 controls turning on and off of the light source 210, and the intensity of the light emitted from each light source, and so on. The light emitted from the light source 210 is guided by a light guide fiber to the illumination window 420 of the rigid scope 400.

The light amount of the light guided to the illumination window 420 of the rigid scope 400 may be adjusted using the intensity of the light emitted by the light source 210, or may be adjusted through other methods. For example, it is possible to provide a diaphragm between the light source 210 and the light incident end of the light guide fiber, and to vary the aperture of the diaphragm to adjust the light amount guided to the rigid scope 400. In order to change the output of the light source 210, power supplied to the light source 210 may be adjusted by varying current values, or by performing pulse width modulation (PWM) control.

The display device 500 is a general display device such as a liquid crystal display. The display device 500 displays images based on the image signals having subjected to the image processing by the later described image processing circuit 120 of the video processor 100.

The video processor 100 comprises the image signal acquisition circuit 110, the image processing circuit 120, the brightness adjustment circuit 130, the control circuit 140, the storage device 150, the input device 160, and the communication circuit 170. The image signal acquisition circuit 110 acquires, from the imaging device 300, image signals generated at the imaging unit 310. The image signal acquisition circuit 110 sends the acquired image signals to the image processing circuit 120.

The image processing circuit 120 performs various image processing on the image signals obtained from the image signal acquisition circuit 110 and outputs the image signals after the image processing to the display device 500. The processing performed by the image processing circuit 120 includes preprocessing 122, detection processing 124, automatic gain control (AGC) 126, and post-processing 128.

In the preprocessing 122, the image signals obtained from the image signal acquisition circuit 110 are subject to color processing, filter processing for noise reduction, gain adjustment processing, etc.

In the detection processing 124, the image signals after the preprocessing 122 are multiplied, for each color, by a detection parameter which is a predetermined coefficient. For example, if an observation mode is a normal light observation (or white light imaging; WLI) mode, the detection parameters for the respective red (R), green (G), and blue (B) colors are set to be R:G:B=0.45:0.45:0.10. In the detection processing 124, a predetermined gain may further be applied. The image signals after the detection processing are sent to the brightness adjustment circuit 130 which will be described later.

In the AGC 126, gain is adjusted for the image signals after the detection processing 124 so that the signal intensity of each color falls in a proper range and the brightness of images becomes appropriate. This gain adjustment is performed under the control of the brightness adjustment circuit 130.

In the post-processing 128, various image processing is performed using the image signals after the AGC 126 to generate images to be displayed on the display device 500. The image signals after the post-processing 128 are sent to the display device 500.

The brightness adjustment circuit 130 adjusts various operations of the endoscope system 10 so that images from the image signals processed by the image processing circuit 120 have an appropriate brightness. The brightness adjustment circuit 130 comprises a photometry unit 131 and a brightness control unit 132. The photometry unit 131 acquires the image signals after the detection processing 124. Based on the acquired image signals, the photometry unit 131 calculates the brightness of images from the image signals. The photometry unit 131 sends the calculation result to the brightness control unit 132.

The brightness control unit 132 changes various settings based on the information on the image brightness obtained from the photometry unit 131. The brightness control unit 132 comprises a light source controller 134, a gain controller 135, and an exposure controller 136.

The light source controller 134 adjusts the output of the light source 210 of the light source device 200 so that images have an appropriate brightness. The light source controller 134 sends the information about the determined output of the light source 210 to the light amount control circuit 230 of the light source device 200. The light amount control circuit 230 controls the operation of the light source 210 based on the information received from the later described control circuit 140 and the output information received from the light source controller 134.

The gain controller 135 determines the gain setting for the AGC 126, as one of the parameters in the image processing performed by the image processing circuit 120 so that the brightness of images becomes appropriate. The gain controller 135 sends the determined gain setting to the image processing circuit 120. The image processing circuit 120 performs the AGC 126 based on the gain setting obtained from the gain controller 135. The gain controller 135 may determine the gain to be applied to the processing other than the AGC 126.

The exposure controller 136 determines the exposure setting of the imaging unit 310 of the imaging device 300 so that images have an appropriate brightness. The exposure controller 136 sends the determined exposure setting to the imaging unit 310. The imaging unit 310 performs imaging operations based on the exposure setting obtained from the exposure controller 136. For example, the exposure time adopted by the imaging unit 310 is based on this exposure setting.

The control circuit 140 takes control over the operation of each unit in the video processor 100. For example, the control circuit 140 is connected to the image processing circuit 120 and the brightness adjustment circuit 130, and issues instructions for the operations of the image processing circuit 120 and the brightness adjustment circuit 130. The control circuit 140 is also connected to the light amount control circuit 230 of the light source device 200, and sends necessary information to the light amount control circuit 230. For example, the control circuit 140 sends information indicative of whether the observation mode is a normal light observation mode or other mode, information indicative of whether the light source 210 should be turned on or turned off, and so on, to the light amount control circuit 230.

Furthermore, the control circuit 140 comprises a determination unit 141. The determination unit 141 determines if a laser mode for performing laser treatment with the laser treatment instrument 600 is adopted, or a normal mode for not performing the laser treatment is adopted, during the observation operation of causing the display device 500 to display the images taken by the imaging device 300 through the rigid scope 400.

The storage device 150 includes, for example, a semiconductor memory, a hard disk, etc. The storage device 150 is connected to the control circuit 140. The storage device 150 may be connected also to the image processing circuit 120, the brightness adjustment circuit 130, etc. The storage device 150 stores a program, set values, etc. required for the operation of each unit.

The input device 160 includes, for example, switches, a keyboard, a touch panel, etc. The control circuit 140 can receive instructions from a user via the input device 160.

The communication circuit 170 is involved in the communications with a laser control device 610 of the laser treatment instrument 600, which will be described later. The control circuit 140 acquires information from a laser control circuit 611 of the laser control device 610 via the communication circuit 170 to obtain the state of the laser treatment instrument 600.

The laser treatment instrument 600 is a treatment instrument used for treating a subject by irradiating the subject with laser light. The laser treatment instrument 600 comprises the laser control device 610 and a laser probe 620. Lasers for treatment are emitted from the tip of the laser probe 620.

The laser control device 610 comprises the laser control circuit 611, a laser drive circuit 612, a laser light source 613, an input device 614, and a communication circuit 615. The laser control circuit 611 controls the operation of each unit in the laser treatment instrument 600. The laser light source 613 is a source of the laser light emitted from the laser probe 620. The laser drive circuit 612 drives the laser light source 613 under the control of the laser control circuit 611. The input device 614 receives inputs to the laser control device 610. The input device 614 may include, for example, switches, a keyboard, a touch panel, etc. Also, the input device 614 comprises a switch for switching on and off the laser light emission from the laser probe 620. This switch may be a foot switch, or a button switch provided at a grip portion for a user to hold the probe. The communication circuit 615 is a circuit for communication with the video processor 100. That is, the communication between the control circuit 140 of the video processor 100 and the laser control circuit 611 of the laser treatment instrument 600 is performed via the communication circuit 170 of the video processor 100 and the communication circuit 615 of the laser control device 610.

The laser light source 613, driven by the laser drive circuit 612 under the control of the laser control circuit 611, emits laser light. This laser light is guided to and emitted from the tip of the laser probe 620. The emission of the laser light here may be continuous, pulse-like, or pulse-repetitive, depending on the setting.

As the laser light source 613 of the laser treatment instrument 600, various light sources may be adopted and interchangeably used. That is, the laser light source 613 may be replaceable, or the laser treatment instrument 600 itself, which is connected to the video processor 100, can be replaced with an instrument comprising a different light source. Here, for example, a holmium:YAG (Ho:YAG) laser, a neodymium:YAG (Nd:YAG) laser, a KTP laser, or the like may be adopted as the laser light source 613. The Ho:YAG laser has a wavelength of 2060 nm, the Nd:YAG laser has a wavelength of 1064 nm, and the KTP laser has a wavelength of 532 nm. As such, the technique according to the present embodiment that aims to control the influence of laser light on observation images serves an important role, especially with the KTP laser having a wavelength in the visible light band.

The image processing circuit 120, the brightness adjustment circuit 130, and the control circuit 140 of the video processor 100 include an integrated circuit such as a central processing unit (CPU), an application specific integrated circuit (ASIC), a field programmable gate array (FPGA), or the like. The image processing circuit 120, the brightness adjustment circuit 130, and the control circuit 140 may be each constituted by a single integrated circuit, etc., or by a combination of multiple integrated circuits, etc. Also, two or more of the image processing circuit 120, the brightness adjustment circuit 130, and the control circuit 140 may be constituted by a single integrated circuit, etc. These integrated circuits are operated, for example, according to a program stored in the storage device 150 or the storage regions in the integrated circuits. The light amount control circuit 230 of the light source device 200 and the laser control circuit 611 of the laser treatment instrument 600 likewise include an integrated circuit, etc.

<Overview of the Treatment>

The overview of the treatment that uses the endoscope system 10 will be described. A user inserts the rigid scope 400 into, for example, a treatment site in an abdominal cavity, etc. By the operations of the imaging device 300 and the video processor 100, images of a subject positioned in front of the rigid scope are displayed on the display device 500. The user can ascertain the state of the subject by looking at the images displayed on the display device 500. The user also inserts the laser probe 620 of the laser treatment instrument 600 into the treatment site. The user manipulates the laser treatment instrument 600 to apply an aiming light to the subject, and to spot the position for the laser light irradiation for treatment while looking at the images displayed on the display device 500. Subsequently, the user manipulates the laser treatment instrument 600 to irradiate the subject as a treatment target with the treatment laser light. In this manner, the treatment with laser light is performed.

<System Operations>

Figure 2:
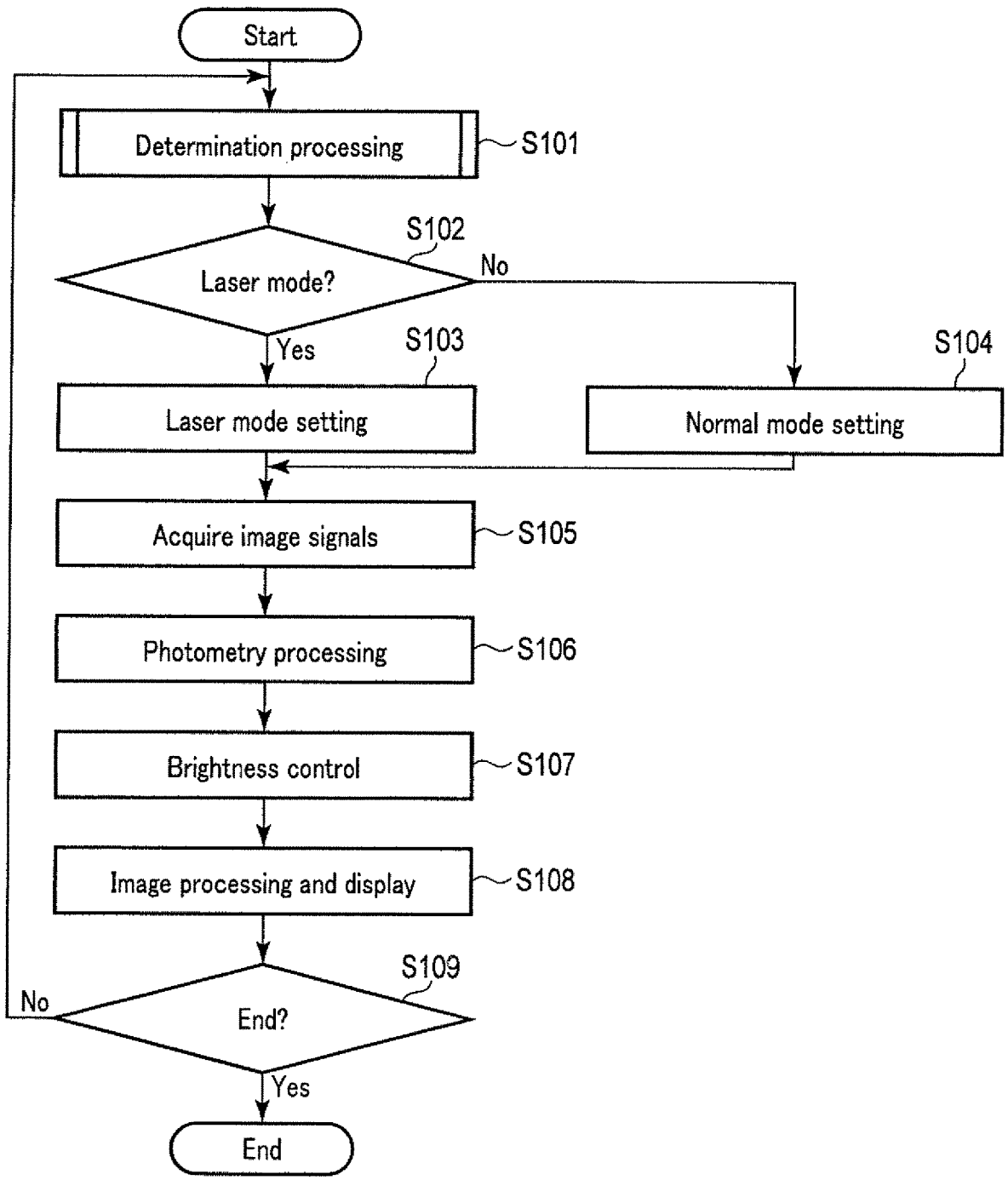
FIG. 2 is a flowchart showing an example of the operation of an endoscope system according to one embodiment.

Descriptions will be given of the operations of the video processor 100 in the endoscope system 10 according to the present embodiment. The endoscope system 10 is equipped with a laser mode and a normal mode, the laser mode using the laser treatment instrument 600 during the observation with the imaging device 300 and the normal mode not using the laser treatment instrument 600. Particularly in the laser mode, various settings are made so that the laser light of the laser treatment instrument 600 does not degrade the quality of observation images. An example of the operation of the endoscope system according to the present embodiment will be described with reference to the flowchart shown in FIG. 2.

Figure 3:
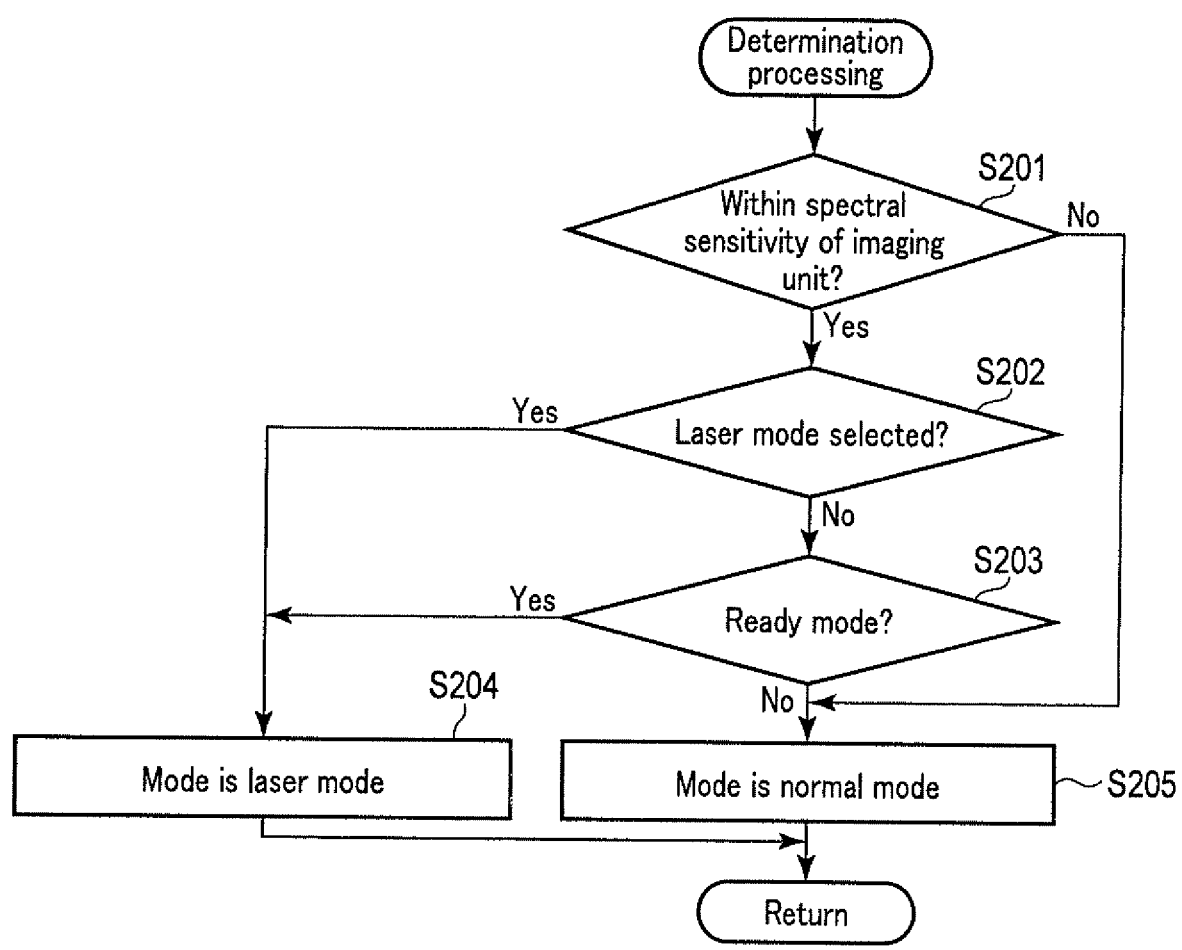
FIG. 3 is a flowchart showing an example of determination processing.

In step S101, the video processor 100 performs determination processing. The determination processing is the processing by the determination unit 141 of the control circuit 140 for determining whether the present mode is the laser mode or the normal mode. An example of the determination processing will be described with reference to the flowchart shown in FIG. 3.

In step S201, the determination unit 141 of the control circuit 140 communicates with the laser control circuit 611 via the communication circuit 170, and determines whether or not the wavelength of laser light from the laser light source 613 of the laser treatment instrument 600 connected to the video processor 100 is within the spectral sensitivity of the imaging unit 310. That is, the determination unit 141 estimates the laser light wavelength. If the laser light wavelength is not within the spectral sensitivity of the imaging unit 310, the processing flow advances to step S205. If the laser light wavelength is within the spectral sensitivity of the imaging unit 310, the processing flow advances to step S202. For example, the processing flow advances to step S202 if the laser light source 613 is a KTP laser or a Nd:YAG laser, and the processing flow advances to step S205 if the laser light source 613 is a Ho:YAG laser.

In step S202, the determination unit 141 determines whether or not a user has selected the laser mode. In this instance, the endoscope system 10 may allow the user to use the input device 160, e.g., a touch panel, to input the information as to whether or not the laser treatment instrument 600 should be used. If information has been input by the user that the laser treatment instrument 600 is used, it is determined that the laser mode has been selected. If the laser mode has been selected, the processing flow advances to step S204. If the laser mode has not been selected, the processing flow advances to step S203.

In step S203, the determination unit 141 determines whether or not the laser treatment instrument 600 is in a ready mode. The laser treatment instrument 600 according to this embodiment is equipped with the ready mode for keeping the laser light source 613 in a standby condition so that laser light can be emitted once an output instruction is made. The determination unit 141 of the control circuit 140 communicates with the laser control circuit 611 via the communication circuit 170 and obtains the information as to whether or not the laser treatment instrument 600 is in the ready mode. If the laser treatment instrument 600 is in the ready mode, the processing flow advances to step S204. If it is not in the ready mode, the processing flow advances to step S205.

In step S204, the determination unit 141 concludes that the mode is the laser mode. Thereafter, the determination processing ends, and the processing flow returns to the main processing that is described with reference to FIG. 2.

In step S205, the determination unit 141 concludes that the mode is the normal mode. Thereafter, the determination processing ends, and the processing flow returns to the main processing that is described with reference to FIG. 2.

Note that the determination in step S201, i.e. determining whether or not the laser light source 613 of the laser treatment instrument 600 is a visible light source, need not be performed each time the determination processing is carried out, but it may be performed only once when the determination processing is carried out for the first time in the series of processing steps.

Turning back to FIG. 2, the description will continue. In step S102, the video processor 100 determines whether or not the present mode is the laser mode. If it is the laser mode, the processing flow advances to step S103. In step S103, the video processor 100 turns each setting of the endoscope system 10 to a laser mode setting. The laser mode setting prevents the substantial degradation in quality of the images displayed on the display device 500, even when the laser treatment instrument 600 emits laser light to the subject in the observation area of the rigid scope 400. The laser mode setting will be detailed later. After the processing in step S103, the processing flow advances to step S105.

In step S102, if it is determined that the mode is not the laser mode, the processing flow advances to step S104. In step S104, the video processor 100 turns each setting of the endoscope system 10 to a normal mode setting. The normal mode setting is a general setting that allows for the display of observation images on the display device 500 with high quality. After the processing in step S104, the processing flow advances to step S105.

In step S105, the video processor 100 acquires image signals. That is, the image signal acquisition circuit 110 acquires the image signals generated by the imaging unit 310, from the imaging unit 310 of the imaging device 300. The image signals are sent to the image processing circuit 120. The image signals are subject to the processing such as color adjustment, noise reduction, gain adjustment, etc. in the preprocessing 122. After the preprocessing 122, the detection processing 124 is performed. By the detection processing 124, the image signals are multiplied by a detection parameter for each color and applied with an appropriate gain. The image signals are then sent to the photometry unit 131 of the brightness adjustment circuit 130.

In step S106, the video processor 100 performs photometry processing. That is, the photometry unit 131 of the brightness adjustment circuit 130 receives the image signals having been subjected to the detection processing from the image processing circuit 120, and performs photometry processing based on the image signals. Specifically, the photometry unit 131 estimates how bright the images currently acquired by the imaging unit 310 are.

In step S107, the video processor 100 performs brightness control based on the result of the photometry processing. That is, the brightness control unit 132 of the brightness adjustment circuit 130 adjusts various parameters so that the images from the image signals will have an appropriate brightness. For example, the light source controller 134 of the brightness control unit 132 adjusts the output of the light source 210 of the light source device 200. The gain controller 135 of the brightness control unit 132 adjusts the gain for the AGC 126 performed at the image processing circuit 120. The exposure controller 136 of the brightness control unit 132 adjusts the exposure of the imaging unit 310 of the imaging device 300.

In step S108, the video processor 100 subjects the image signals acquired at the imaging device 300 to the image processing that is commensurate with the brightness control, and displays the images after the image processing on the display device 500. That is, the image processing circuit 120 of the video processor 100 performs the image processing including the AGC 126 under the control of the brightness control unit 132. The image processing circuit 120 outputs the image signals after the image processing to the display device 500 for the display device 500 to display the images.

In step S109, the video processor 100 determines whether or not to terminate the processing flow. If the termination is not determined, the processing flow returns to step S101 to repeat step S101 to step S109. If the termination is determined, the processing flow ends. The processing of step S101 to step S109 concurs with the timing of the field for imaging in the imaging unit 310, and repeats field by field.

<Regarding the Laser Mode Setting>

The laser mode setting concerned in step S103 will be described. A number of methods are available for preventing the substantial degradation in quality of images displayed on the display device 500 even when the laser treatment instrument 600 emits laser light to a subject in the observation area of the rigid scope 400. Hereinafter, descriptions of the settings in such methods will be given respectively.

[First Method]

Figure 4:
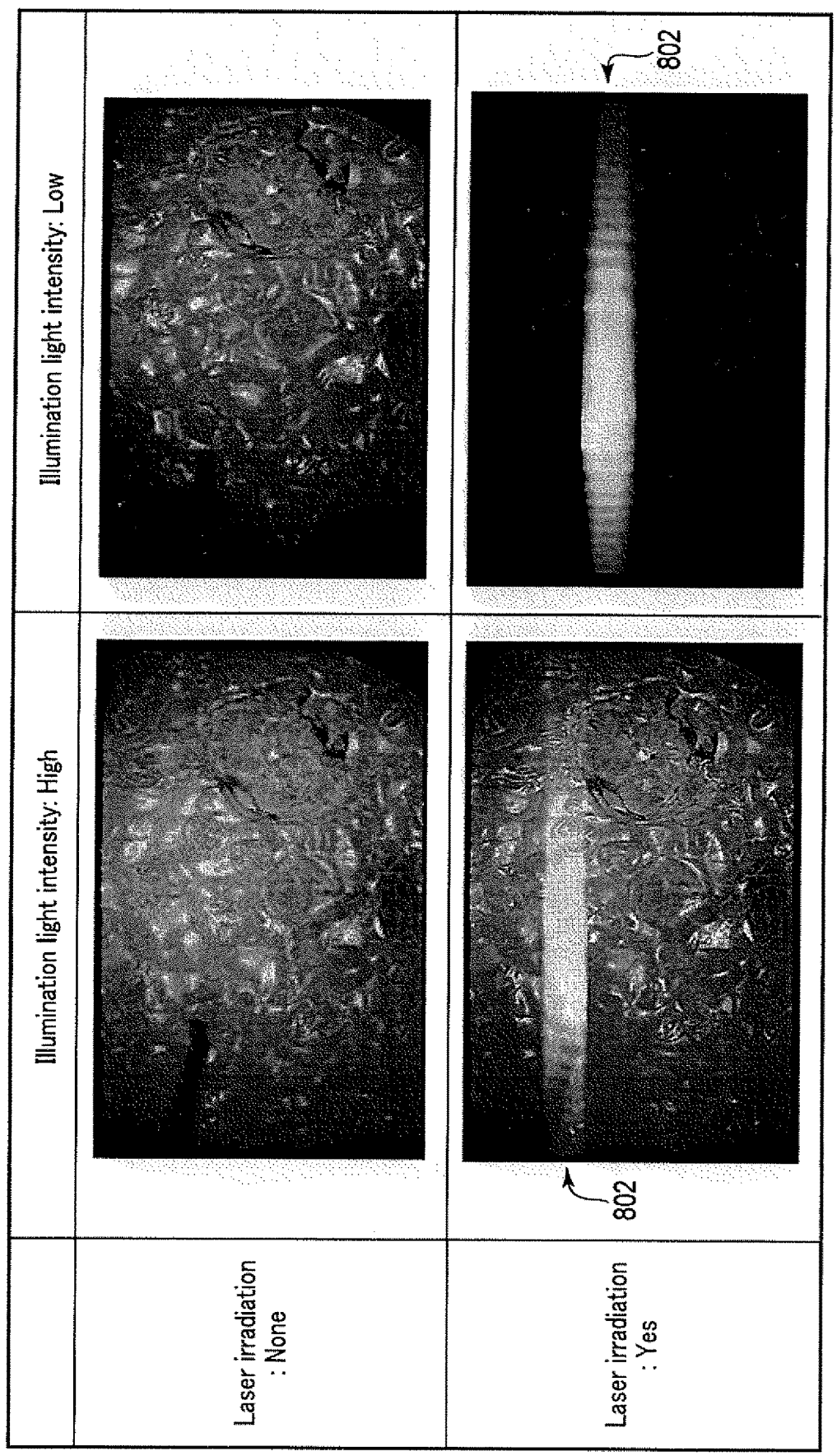
FIG. 4 shows certain examples of images displayed on a display device.

The first method for controlling the influence of laser light irradiation on the quality of displayed images is a method to increase the amount of illumination light emitted from the light source device 200. FIG. 4 shows certain examples of images displayed on the display device 500 for the respective cases of conducting, and not conducting, the laser irradiation by the laser treatment instrument 600 while illumination light is applied with a high intensity and a low intensity. In FIG. 4, the images in the left column are when the intensity of illumination light is high, and the images in the right column are when the intensity of illumination light is low. In FIG. 4, the images in the upper row are when the laser irradiation is absent, and the images in the lower row are when the laser irradiation is present.

Looking at the upper row in FIG. 4, the images obtained when the laser irradiation is absent are not very different from each other, irrespective of the high intensity or the low intensity of the illumination light. Changes in the intensity of illumination light do not affect the final images because, for example, the exposure conditions are adjusted for the imaging unit of the imaging device 300, the gain is adjusted in the image processing circuit 120 of the video processor 100, and so on.

On the other hand, in the lower row in FIG. 4 for the cases with the presence of laser irradiation, the image obtained when the intensity of illumination light is high includes a thin band 802 originated from the laser light, whereas the image obtained when the intensity of illumination light is low includes a thick band 802 originated from the laser light. Also, in these images, the observation target in the regions other than the band 802 is brightly shown and easily recognized when the intensity of illumination light is high, whereas the observation target in the regions other than the band 802 is darkly shown and hardly recognized when the intensity of illumination light is low. Such results are assumed to be attributable to the effect that an S/N ratio is improved by increasing the intensity of the illumination light emitted on the observation target with respect to the laser light, the laser light being regarded as noise for an observation image.

In the first method according to this embodiment, the output of the light source 210 in the laser mode setting is set to, for example, a maximum value. Then, in order to obtain an appropriate brightness, the exposure conditions for the imaging unit 310 and the conditions of the image processing in the image processing circuit 120 are adjusted.

With this method, the substantial degradation in quality of images displayed on the display device 500 can be prevented even when the laser treatment instrument 600 emits laser light to a subject in the observation area of the rigid scope 400.

[Second Method]

The second method for controlling the influence of laser light irradiation on the quality of displayed images is a method to use an electronic shutter so that the exposure time in the imaging by the imaging unit 310 is shortened. When a subject is irradiated with laser light, excessive exposure as compared to proper exposure tends to occur since the scattering, etc. of the laser light makes the whole imaging range bright. For example, images can easily have blown-out highlights. Accordingly, the exposure time is shortened by an electronic shutter to give a proper exposure value.

Figure 5B:
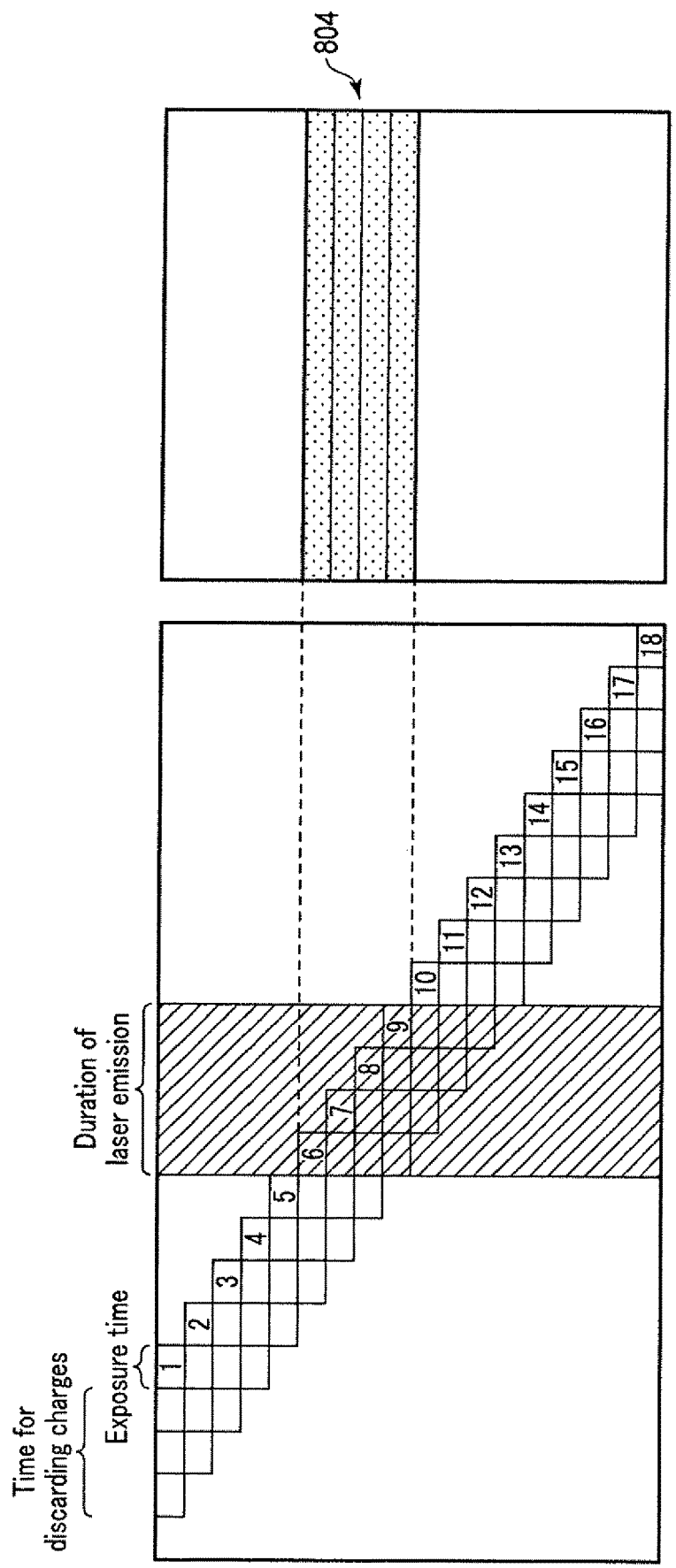
FIG. 5B is an illustration for explaining the effect of an electronic shutter when an image sensor is a CMOS image sensor. The figure serves to explain the relationship between exposure time and a read image when the exposure time is short.

Moreover, when the image sensor comprised by the imaging unit 310 is a CMOS image sensor, the following effect is obtained. With reference to FIG. 5A and FIG. 5B, the effect of the electronic shutter in the case with a CMOS image sensor will be described. FIG. 5A shows the relationship between exposure time and a read image when the exposure time is long, and FIG. 5B shows the relationship between exposure time and a read image when the exposure time is short.

With a CMOS image sensor, charges accumulated in light receiving elements from received light are sequentially read line by line using the so-called rolling shutter technique. For example, as shown in FIG. 5A, the timing of exposure is different for each line, and the exposure may be sequentially performed from the top to the bottom, followed by sequential reading. In this instance, if pulse-type laser light irradiation by the laser treatment instrument 600 is conducted, a band 804 originated from the laser light would appear on the portion corresponding to the lines exposed at the timings of the laser light irradiation.

Comparing FIG. 5A for the case of long exposure time and FIG. 5B for the case of short exposure time, it can be understood that FIG. 5B for the short exposure time shows a narrower band 804 originated from the laser light and also shows a lower brightness. The second method uses an electronic shutter to shorten the exposure time in the imaging by the imaging unit 310, in the expectation of such an effect.

With this method, the substantial degradation in quality of images displayed on the display device 500 can be prevented even when the laser treatment instrument 600 emits laser light to a subject in the observation area of the rigid scope 400.

If the amount of illumination light of the light source device 200 is adjusted by the pulse width modulation control while an electronic shutter is used, a stripe will appear in the images due to the same principle as that caused the band 804 that originated from the laser light, as discussed above. Therefore, when an electronic shutter is used, the pulse width modulation control should be avoided in controlling the light source 210.

Figure 6:
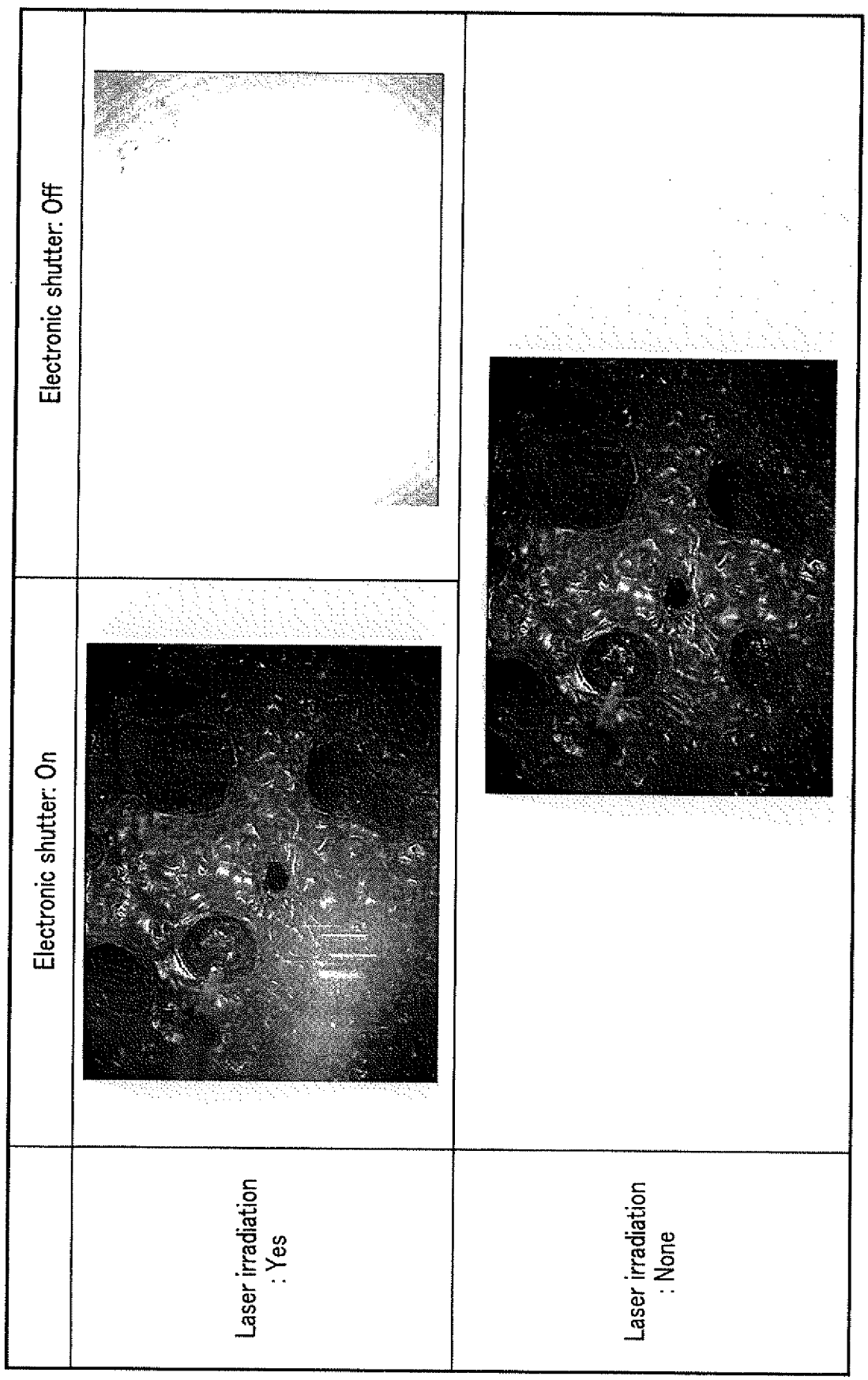
FIG. 6 shows certain examples of images displayed on a display device.

Descriptions have been given of the case of using a CMOS image sensor, but shortening the exposure time by use of an electronic shutter is likewise effective in the case of using a CCD image sensor. FIG. 6 shows certain examples of images displayed on the display device 500 when a CCD image sensor is used. The upper row in FIG. 6 is when the laser irradiation is present, and the lower row in the figure is when the laser irradiation is absent. The left column is when the electronic shutter is on, and the right column is when the electronic shutter is off. As shown in FIG. 6, when the electronic shutter is off, the entire image is subject to blown-out highlights due to the scattering of the emitted laser light. On the other hand, when the electronic shutter is on, the effect of suppressing blown-out highlights has been obtained.

Additionally, in the case of using a CCD image sensor, if the amount of illumination light of the light source device 200 is adjusted by the pulse width modulation control while an electronic shutter is used, hunting will occur due to the difference in timing between the exposure times by the electronic shutter and the pulse width modulations on the illumination light. Therefore, in the case of also using a CCD image sensor, the pulse width modulation control should be avoided in controlling the light source 210 when an electronic shutter is used.

[Third Method]

The third method for controlling the influence of laser light irradiation on the quality of displayed images is a method that adopts both the first method of increasing the amount of illumination light and the second method of using an electronic shutter to shorten the exposure time. From such combination, it is also possible to obtain the same effects as described above for the first method and the second method.

<Regarding the Brightness Control>

With reference to FIG. 7 as a schematic diagram, descriptions will be given of the overview of an exemplary control of each unit in the endoscope system 10 when controlled according to the third method above. In each drawing in FIG. 7, the horizontal axis represents time. It will be assumed that the laser treatment instrument 600 does not output a laser during the periods indicated as (1) and (2) at the bottom of FIG. 7, while the laser treatment instrument 600 is outputting a laser during the period indicated as (3) at the bottom of FIG. 7. That is, operations in the normal mode are being performed during the periods (1) and (2), while operations in the laser mode are being performed during the period (3). It will also be assumed that the output of the light source 210 is low and the light source 210 is under the pulse width modulation control during the period (1), while the light source output is increased to some degree and the light source 210 is under the current value control during the period (2).

The first drawing (a) from the top of FIG. 7 shows the pulse width of the output of the light source 210 with respect to time. The pulse width being 100% indicates that the illumination light is continuously emitted, and the pulse width being less than 100% indicates that the pulse width modulation control is performed.

The second drawing (b) from the top of FIG. 7 shows the drive current of the light source 210 with respect to time. It shows that the light source 210 is under the pulse width modulation control during the period (1) where the drive current exhibits the minimum value, and the light source 210 is under the current value control during the period (2) where the pulse width is 100%. During the period (3) where the laser is being emitted, the output of the light source 210 is set to be the maximum.

The third drawing (c) from the top of FIG. 7 shows the exposure time of the imaging unit 310 with respect to time. During the periods (1) and (2) where the laser is not emitted, the exposure time is set to be long. During the period (3) where the laser light is being emitted, the exposure time is set to be short.

The fourth drawing (d) from the top of FIG. 7 shows the brightness of a final image with respect to time. Throughout the periods (1) and (2) where the laser it not emitted as well as the period (3) where the laser light is being emitted, the brightness of the image is kept at the proper value.

<Advantage of the System>

According to the present embodiment, at least one of the exposure time in the imaging by the imaging unit 310 and the amount of the emitted light of the light source 210 is adjusted in accordance with the state of use of the laser treatment instrument 600. Therefore, even if a subject is irradiated with the illumination light and the laser light at the same time, observation images can be obtained with high quality.

<Modifications>

Certain modifications of the above embodiment will be described.

In the above embodiment, whether or not the laser is a visible-light laser is determined in step S201, and if the laser is not a visible-light laser, the normal mode is set. However, the present invention is not limited to this. As one example, the extent of setting may be changed in accordance with the degree of influence which the employed laser would impose on the visible light band. For example, as the influence on the visible light band increases, the exposure time may be shortened by an electronic shutter, the output of the light source 210 may be increased, the gain of the AGC 126 may be reduced, or their combination may be performed. The degree of the laser's influence on the visible light band can be estimated, for example, in accordance with the wavelength of laser light.

Moreover, the processing described with reference to the flowchart can be modified as appropriate. Some of the processing may be omitted or performed in a different order, or other processing may be added. For example, it is possible to omit some of the determinations in the determination processing steps S201 to S203 described with reference to FIG. 3.

In the above embodiment, the endoscope system 10 using the rigid scope 400 and the imaging device 300 has been described as an example, but the present invention is not limited to this. The techniques described are applicable also to flexible scopes configured to transmit optical images through optical fibers. Moreover, the techniques described are applicable to, for example, electronic endoscopes comprising an image sensor at the end portion, as well. Such electronic endoscopes may be flexible scopes or rigid scopes. Moreover, the techniques described are applicable to not only endoscopes, but also other devices such as fluorescence microscopes.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope system comprising:
a light source configured to emit illumination light for illuminating a subject;
an imager comprising an image sensor configured to image the subject using illumination light reflected off of the subject, a wavelength of the illumination light being within a spectral sensitivity of the imager;
a laser treatment instrument including a laser light source which is configured to emit laser light for treating the subject during emission of the illumination light;
a control circuit configured to determine whether or not a wavelength of the laser light is within the spectral sensitivity of the imager, and a state of operation of the laser treatment instrument, by communicating with the laser treatment instrument; and
a brightness adjustment circuit which adjusts a brightness by at least one of shortening exposure time in imaging by the imager and increasing an amount of emitted light of the light source when the wavelength of the laser light is within the spectral sensitivity of the imager and the laser treatment instrument is emitting laser light.

2. The endoscope system according to claim 1, wherein if the exposure time in imaging by the imager is adjusted by an electronic shutter, the brightness adjustment circuit causes the light source to adjust the amount of emitted light based on current value control.

3. The endoscope system according to claim 1, wherein if the brightness adjustment circuit has caused the imager to shorten the exposure time, the brightness adjustment circuit causes the light source to set the amount of emitted light to a maximum.

4. The endoscope system according to claim 1, further comprising:
an input device configured for an input as to whether or not a user uses the laser treatment instrument,
wherein the control circuit determines the state of operation of the laser treatment instrument based on the input to the input device.

5. The endoscope system according to claim 1, further comprising:
a first casing containing the light source; and
a second casing different from the first casing, the second casing containing the laser light source.

6. The endoscope system according to claim 1, wherein the laser light is a neodymium:YAG (Nd:YAG) laser, or a KTP laser.

* * * * *